United States Patent [19]

Carlson

[11] 4,359,056
[45] Nov. 16, 1982

[54] AUTOMATIC DIGITAL BACKFAT METER

[75] Inventor: David L. Carlson, Ames, Iowa

[73] Assignee: Renco Corporation, Minneapolis, Minn.

[21] Appl. No.: 223,481

[22] Filed: Jan. 8, 1981

Related U.S. Application Data

[63] Continuation-in-part of Ser. No. 162,319, Jun. 23, 1980.

[51] Int. Cl.³ .................................................. A61B 10/00
[52] U.S. Cl. ..................................... 128/660; 73/631
[58] Field of Search ................. 128/660–661; 73/609–617, 631

[56] References Cited

U.S. PATENT DOCUMENTS

| | | | |
|---|---|---|---|
| 3,041,872 | 7/1962 | Brown et al. | 73/612 |
| 3,053,080 | 9/1962 | Cotten et al. | 73/611 |
| 3,555,889 | 1/1971 | Weighart | 73/612 |
| 3,565,057 | 2/1971 | Hart | 128/661 |
| 3,818,898 | 6/1974 | Williams | 128/660 |
| 3,827,287 | 8/1974 | Boggs et al. | 73/609 |
| 3,828,768 | 8/1974 | Douglas | 128/702 |
| 3,872,858 | 3/1975 | Hudson et al. | 128/660 |
| 3,888,238 | 6/1975 | Meindl et al. | 128/663 X |
| 3,921,622 | 11/1975 | Cole | 128/660 |
| 3,964,297 | 6/1976 | Jorgensen et al. | 73/609 |
| 3,972,228 | 8/1976 | Mansson | 73/609 |
| 4,030,343 | 6/1977 | Lund et al. | 73/610 X |
| 4,111,054 | 9/1978 | Jorgenson et al. | 73/611 |
| 4,112,927 | 9/1978 | Carlson | 128/660 |
| 4,138,999 | 2/1979 | Eckhardt et al. | 128/660 |

FOREIGN PATENT DOCUMENTS 7915059  9/1979  Fed. Rep. of Germany.

*Primary Examiner*—Robert W. Michell
*Assistant Examiner*—Francis J. Jaworski
*Attorney, Agent, or Firm*—Merchant, Gould, Smith, Edell, Welter & Schmidt

[57] ABSTRACT

An automatic digital backfat meter. An apparatus and method primarily for measuring the thickness of backfat in an animal which automatically adjusts sensitivity and notifies the user when a proper reading is obtained. The transducer (62) produces pulses which pass amplifier (64), threshold detector (68), and are counted in counter (74). If two counts are received, indicator (76) is activated. If two counts are not received, the cycle is repeated and the amplifier (64) has its gain increased by sensitivity control (66) in a stepwise increment until the first fat layer is detected. Time delay (78) prevents the first echo from being counted at counter (74).

10 Claims, 6 Drawing Figures

AUTOMATIC DIGITAL BACKFAT METER

This is a continuation-in-part of my co-pending patent application Ser. No. 162,319, filed June 23, 1980.

Technical Field

The present invention relates to ultrasonic measuring apparatus, in particular a testing device for measuring the depth of backfat found on livestock.

BACKGROUND OF THE INVENTION

In the livestock industry and most importantly in the raising of hogs, it is important to determine the amount of backfat on an animal. Previously, this measurement was obtained by piercing the skin of the animal with a mechanical measuring tool. This mechanical method was undesirable due to the irritation and possible infection which the animal might suffer, and in some areas, this method has been made illegal. As an alternative, ultrasonic waves can be transmitted into the animal, and by measuring reflected echoes, the depth of various fat layers can be determined. Because such animals have various layers of tissue and fat, a single ultrasonic pulse transmitted into the animal produces multiple return echoes originating at the interface between such layers. The problem, therefore, unsolved by prior art devices, was to isolate the desired reflective pulses or echoes from unwanted echoes and produce an output display in a directly readable form which would immediately supply the measurement data without operator interpretation. Prior art devices have used oscilloscope displays to display all reflected pulses, leaving the problem of interpreting which pulses are relevant and calculating the thickness measurement of the device to the operator.

The present invention improves over the prior art by providing a scheme which is capable of discriminating between various layers of skin and backfat in order to locate the appropriate layer and convert that information to a digital readout in terms of units of length, which can be understood immediately by the operator without further interpretation. Furthermore, the present invention provides a warning indicator to notify the operator that the apparatus has located the appropriate backfat layer so that the operator knows that the data appearing at the readout is accurate. Finally, the present invention performs these tasks without the need for calibration by the operator.

SUMMARY OF THE INVENTION

The present invention discloses a method and apparatus for ultrasonic measurement of backfat thickness in animals including a means for transmitting ultrasonic energy pulses and for receiving return echoes, including a probe for placement on the body of an animal to be tested and means for detecting the $n^{th}$ one of n strongest echo pulses from a given transmitted pulse, where n is a predetermined number corresponding to the number of fat layers in the animal to be tested. The present invention also includes measurement and display means responsive to the detecting means for measuring the travel time of the $n^{th}$ echo pulse and for displaying the travel time in terms of depth within the animal's body of the layer corresponding to the inner fat layer.

According to one aspect of the invention, the responsiveness of the apparatus is continually increased on succeeding transmitted pulses (by increasing transmitted power or increasing receiver sensitivity) until the first fat layer is detected. When the desired fat layer is detected, the thickness is measured and indicated.

DETAILED DESCRIPTION OF THE INVENTION

Figure 1:
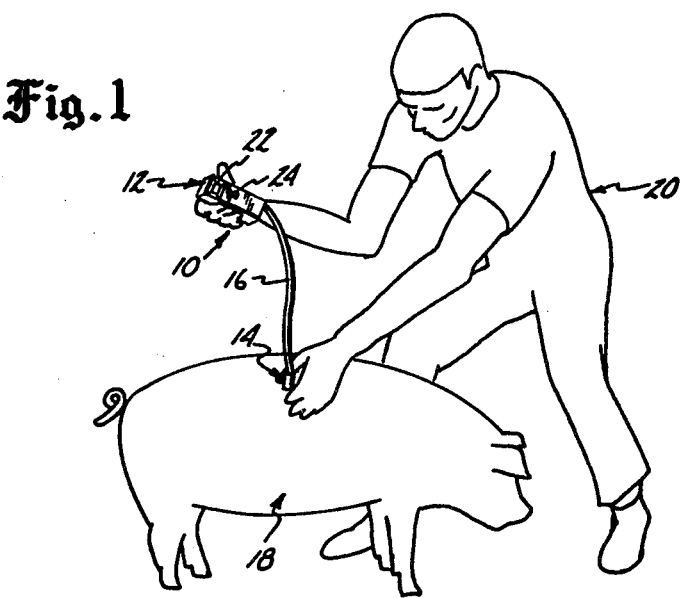
FIG. 1 is a perspective view showing the present invention in a typical testing situation on an animal.

Referring to the drawings, wherein like numerals represent like parts throughout the several views, the present invention, designated generally as 10 in FIG. 1, includes a hand-held unit 12, an ultrasonic probe 14 and a flexible connecting cable 16 therebetween. In FIG. 1, the invention is shown in a typical operating situation where probe 14 is placed on pig 18 by operator 20. Unit 12 includes a digital readout display 22 which in the preferred embodiment displays the desired information in millimeters. The unit also has an indicator lamp 24 which, when lit, indicates the proper operation of the present invention, as will be explained in greater detail hereinafter.

It is known that ultrasonic pulses, when transmitted into the body of an animal, will return echoes or return pulses due to reflection at the interfaces between various layers of animal tissue. Using this principle, the present invention automatically selects the desired return pulses and converts that information into a distance measurement in a directly readable form.

Figure 2:
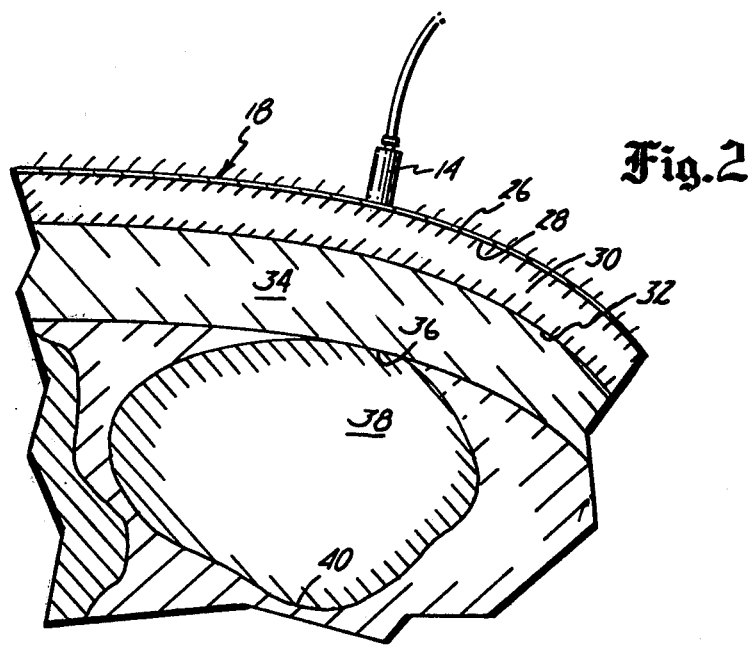
FIG. 2 is a sectional view through a portion of the animal's back with the probe in place.

In order to understand the operation of the invention, reference should be had to FIG. 2, which illustrates a typical cross-sectional view of the biological structure of a pig. Ultrasonic probe 14 is shown applied firmly against the outer skin 26 of the animal. Just below the skin is a first interface 28 between the first layer of backfat 30 and the skin 26. At the end of the first backfat layer there is a second interface 32 which delineates the beginning of the second layer of backfat 34. A third interface 36 generally occurs between layer 34 and the loin muscle 38. Finally, there is a fourth interface 40 where the loin muscle ends. Although the distances vary substantially, layer 30 may average 10 millimeters in thickness, layer 34 may be approximately 20 millimeters thick, and the loin muscle 28 may be 120 millimeters across. Of course, these dimensions will vary greatly from animal to animal. Some species of swine may have more than 2 layers of fat, and accordingly there will be an additional interface. The present invention can be modified to make backfat measurements on these species, as explained hereinafter.

Figure 3:
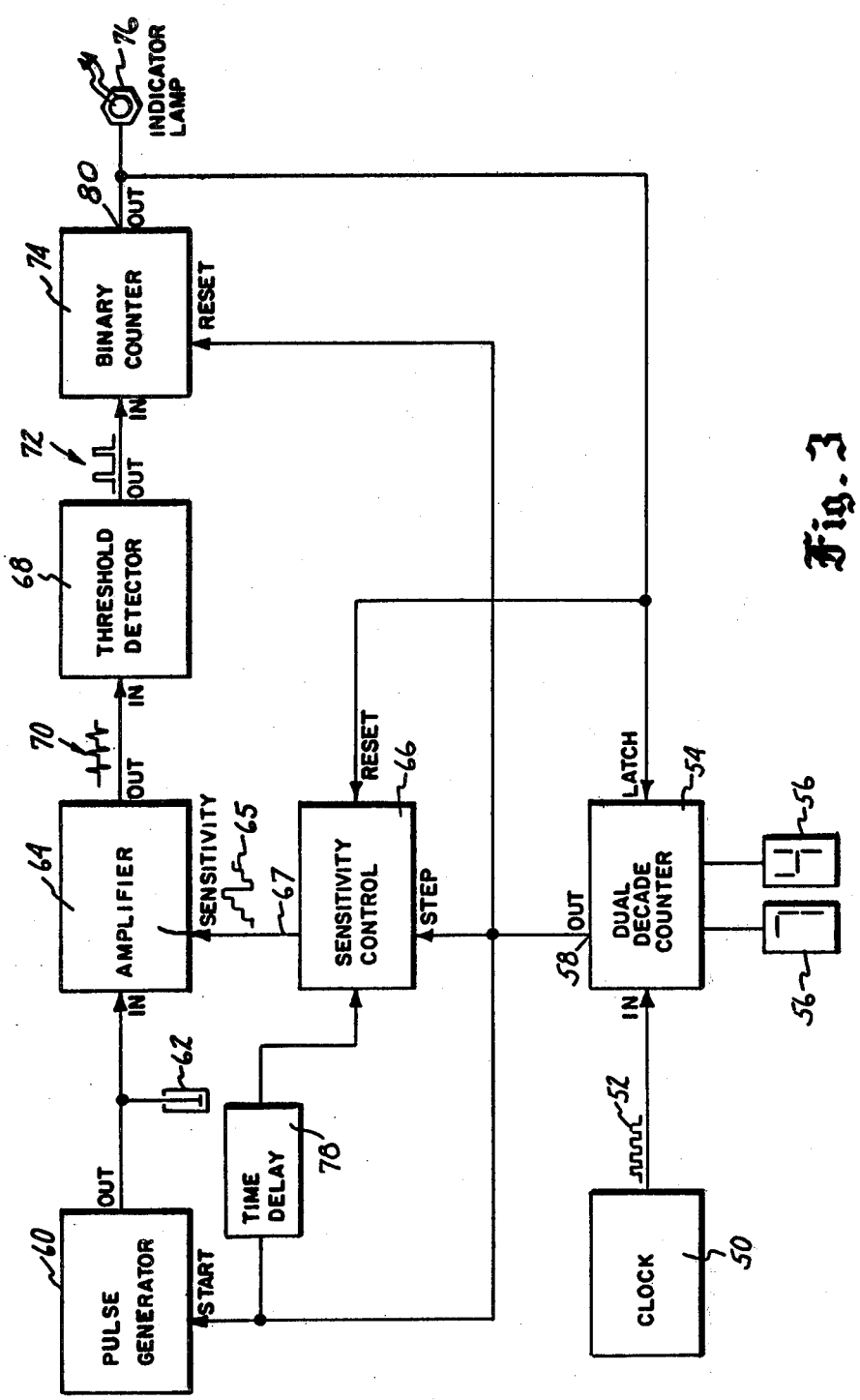
FIG. 3 is a flow diagram of the present invention.

FIG. 3 illustrates in block diagram form the functional operation of the invention. A clock 50 generates a pulse train of square wave pulses 52 which are transmitted to a dual decade counter 54. Counter 54 is shown as a dual decade counter, as only two displays are employed; however, in the preferred embodiment a quad-decade counter (count to 10,000) is employed in order to pulse probe 14 less frequently, thereby minimizing the energy consumption of the unit. The operation of the invention is essentially unchanged, however. The oscillating frequency of the clock 50 is scaled such that the output of the counter shown here as display elements 56 will read directly into millimeters. Each pulse into counter 54 causes the counter to advance one unit. When the counter overflows (i.e., to a count of 100) an output at 58 is produced which is transmitted to pulse generator 60. This generator applies a DC pulse to the ultrasonic transducer 62 which is enclosed within probe 14. When a transmitting pulse is sent through transducer 62, the input to amplifier 64 is temporarily cut off to prevent amplifier overload (not shown in block diagram). When the return pulses or echoes are received at transducer 62 they are then amplified at amplifier 64. The sensitivity or gain of amplifier 64 is controlled by a sensitivity control 66 which is a stepwise incremental control which can increase the gain factor of the amplifier 64 by discrete increments. Wave form 65 above control 66 shows a stylized step output of the control (See FIG. 5 line B for actual trace). A shift register may be used to generate this form. The sensitivity control 66 is caused to increase to the next higher increment whenever an output pulse appears at 58 from counter 54. The connection is shown by line 67.

The output of amplifier 64 is connected to a threshold detector 68 which performs two functions. The first being to convert return pulses which appear at its input as AC pulses, such as those designated 70, to DC pulses at the output, such as those designated by the numeral 72. The second purpose of detector 68 is to act as a filter to prevent or suppress the passage of pulses which do not exceed a predetermined minimum level.

The output of detector 68 is then fed into a binary counter 74 which counts consecutive pulses. When two consecutive pulses have been counted, the counter produces an output signal to an indicator light 76. It should be noted that indicator 76 could take the form of an audible warning or other means to notify the user. With indicator 76 activated, the user is informed that two pulses have been received which have passed through the threshold detector 68. As will be explained hereinafter, when indicator 76 is lit, the user is informed that the apparatus is showing on display 56 the measurement in millimeters of the distance from probe 14 to third interface 36. Although shown in discrete blocks, amplifier 64, detector 68, and counter 74 can also be considered as a single pulse detecting circuit.

Figure 4:
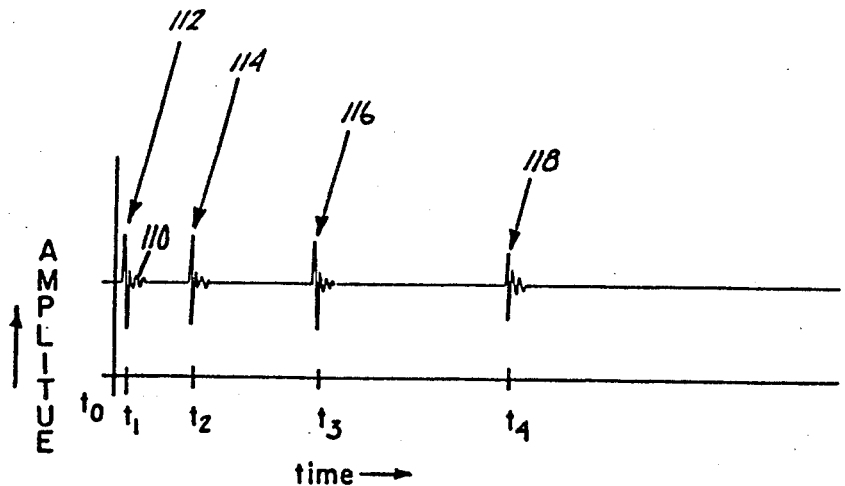
FIG. 4 is a graph showing a typical response recording the reflected pulses from the transducer.

In order to understand the remainder of the flow graph in FIG. 3, reference should be had to the next figure. FIG. 4 is a graph illustrating typical return pulse wave forms which would be detected at probe 14 after transmitting an ultrasonic pulse into an animal. At time 0, a pulse would be transmitted. A short time thereafter at time $T_1$, the first echo 112 reflecting off the outer skin 26 would be received. Sometime later, at time $t_2$, for example, a second return pulse would be received from waves reflected at interface 32. At $t_3$, a reflected pulse 116 from interface 36 would be received. At $t_4$, a pulse 118 would be received from interface 40. In order to determine the thickness of backfat of the animal, the time from $t_0$ to $t_3$ must be determined.

Since the tissue is not absolutely homogeneous, reflected echoes do not return as pure or clean as the transmitted pulse. The echo reflected off the first interface is a particular problem in that it is very strong and the homogeneity of the interface returns additional echoes (as indicated by 110) which trail the primary echo 112. Echoes 110 may themselves be of sufficient amplitude to be mistakenly counted as reflections of later interfaces. It is necessary, therefore, to cause amplifier 64 to ignore the echoes 110 and 112 altogether. To accomplish this, a fixed time delay 78 is employed to reset sensitivity control 66 to minimum sensitivity for a predetermined period of time, which in turn lowers the gain of amplifier 64. With the gain lowered, echoes 110 and 112 will not pass through detector 68 and thus counter 74 will ignore those pulses. When an output appears at 58 of counter 54, the pulse generator is pulsed and time delay device 78 is started. For the predetermined period, time delay 78 holds sensitivity control 66 to minimum sensitivity. At the end of the time period, sensitivity control 68 returns to its previously set level. By using a time delay of approximately 3 to 5 microseconds, the echo received from the first interface will be effectively ignored by counter 74.

Like echo 112, remaining echoes 114, 116, and 118 are also closely followed by multiple minor echoes of lesser amplitude such as 110. If the gain of amplifier 64 was set to high, the minor echoes might be interpreted by counter 74 as echoes from later interfaces. Therefore it is necessary to keep the amplifier 64 at a minimum sensitivity such that it is sensitive enough to read the large spike but not too sensitive so as to count the minor echoes as additional return echoes. In order to accomplish this, sensitivity control 66 is configured to stepwise increase the level of sensitivity or gain factor in the amplifier. Initially, control 66 is set to its lowest level. However, every time output 58 appears control 66 is caused to step to the next higher sensitivity or level of gain. Thus, every time pulse generator 60 transmits a pulse, amplifier 64 is incremented by a control 66. If counter 74 does not reach a count of "2" before counter 54 overflows (count to 100 on a dual decade or count to 10,000 on a quad decade), the counters and sensitivity control 66 are reset and pulse generator 60 is reactivated. At some point, amplifier 64 will have sufficient gain to produce a signal of sufficient magnitude to pass through threshold detector 68 and be counted by counter 74. When counter 74 reaches a count of 2, it produces an output at 80 which resets control 66 to its minimum sensitivity level. Output 80 is also fed into the latch control of counter 54 which causes the counter to freeze its count and display its data in digital display 56. Thus, when two pulses are received at output 80, indicator light 76 is activated and display 56 indicates the distance in millimeters to the third interface 36.

As an alternative to the configuration of the preferred embodiment, it is possible to have sensitivity control 66 control the threshold level of detector 68 rather than the gain of amplifier 64. The result at counter 74 will be the same. It would also be possible to have sensitivity control 66 adjust the output pulse power of generator 60. Again, the result at counter 74 would be the same in terms of controlling sensitivity.

Figure 5:
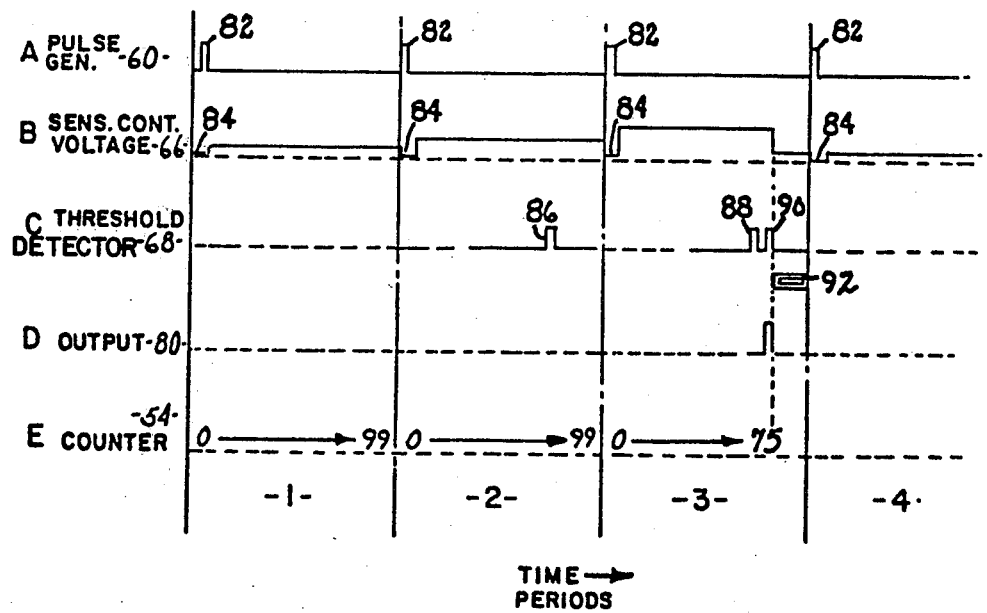
FIG. 5 is a multiple trace graph illustrating the electrical operation of the present invention.

FIG. 5 illustrates the operation of the present invention in terms of pulses over a period of time which might be read at certain points in the circuit. On trace A, the pulses from pulse generator 60 are plotted against time. DC pulses 82 appear periodically according to output 58 of counter 54. The trace B indicates this stepwise incrementing of the sensitivity control 66 and thereby the gain factor of amplifier 64.

Trace B is a plot of output of sensitivity control 66 indicating relative voltage as plotted against time. After each pulse 82 of the pulse generator, there is a period 84 where the sensitivity control 66 is set at its minimum predetermined level due to the action of time delay 78. After this time period has passed 84, the sensitivity is stepped up. In the first period, sensitivity is stepped to the first increment and in successive periods the sensitivity voltage is stepwise increased.

Looking to trace C, which illustrates relative voltage at the output of threshold detector 68 as plotted against time, it can be seen that in the first period, no echo or return pulse has sufficient magnitude to pass through the predetermined level of threshold detector 68. Only after the sensitivity control 66 is incremented do any of the echoes have sufficient amplitude to pass through the threshold detector. Pulse 86 appears sometime in period 2 indicating an echo at interface 32. In period 3, pulses 88 and 90 succeed in passing threshold detector 68 because sensitivity control 66 has been incremented one more step. Once pulse 90 has been received by counter 74 indicator light 76 will be activated as shown by the shaded portion 92 following pulse 90. It should also be noted that with indicator 76 activated, counter 54 is latched. Sensitivity control 66 and counter 74 are reset at the beginning of period 4 when counter 54 produces an output at 58.

Trace D in FIG. 5 plots relative voltage versus time at output 80 of counter 74. A pulse appears at the end of period 3 indicating that two counts have been received in counter 74. At that point counter 54 is latched and an output appears fixed at display 56. Counter 54 continues to count to overflow although the count at display 56 is fixed for the remainder of the period. At the end of each period counter 74 is reset by the pulse appearing at output 58.

Trace E in FIG. 5 illustrates the count in counter 56 plotted against time. In periods 1 and 2, the counter will start from 0 and go to 99 (or 9,999 for a quad decade counter) at the end of the period whereupon an output at 58 will appear and a new pulse will be generated. The counter 54 will then also start from 0 again. In the third period, however, an output will appear at 80 in counter 74 which will latch counter 56 at a count of perhaps "75". Thus, the numeral "75" on the graph indicates that display 56 would show the counter stopped at 75 mm.

In operating the device, the user places probe 14 against the outer skin 26 of the animal. A lubricant such as oil or water may be used to ensure good contact between skin 26 and the probe 14. The unit may then be activated by an external switch (not shown) which starts clock 50 which in turn activates the remaining circuitry in the sequence as discussed above. The user simply holds the probe steady and waits until indicator light 76 appears. Once the light is activated, the display 56 will indicate the distance from the outer skin 26 to the third interface 36 in millimeters. Indicator 76 will appear to be a steady light; however, it will actually be a pulsating light of high frequency indicating successive measurements are being made.

It is possible to alter the present invention to measure the distance from outer skin 26 to any of the other interfaces by modifying the number of counts counter 74 must reach in order to produce an output 80 or alternatively to lengthen or shorten time delay 78. Because of sensitivity control 66 which automatically adjusts the sensitivity of amplifier 64, the user need not calibrate the device to receive an accurate reading.

The present invention may be practiced as an apparatus or a method which performs in the manner as described herein.

Figure 6:
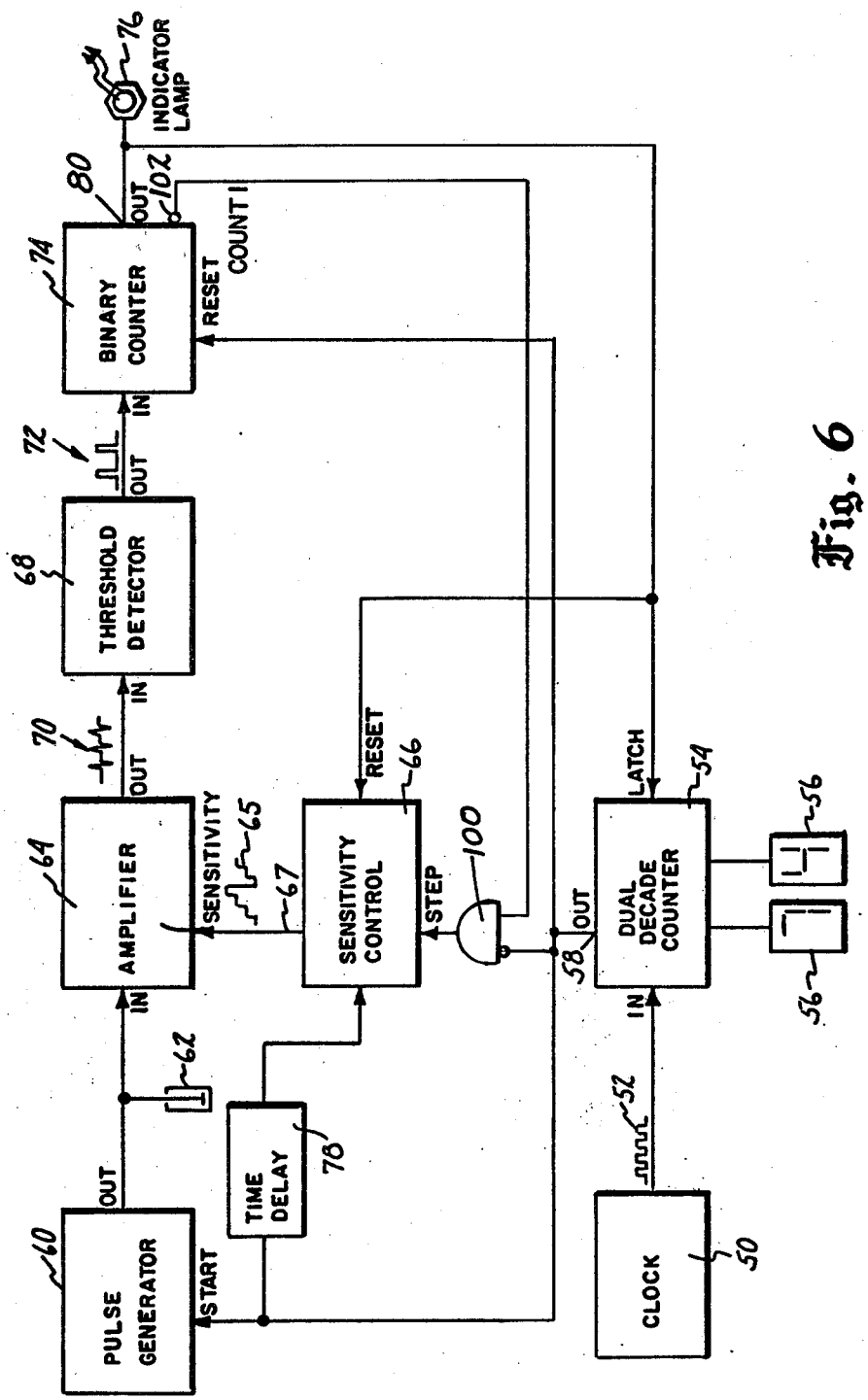
FIG. 6 is a block diagram, similar to FIG. 3, of a further embodiment of the invention.

An improvement to the preferred embodiment as shown in FIG. 3, can be seen in FIG. 6. Most components of FIG. 6 are identical to those of FIG. 3, and have the same reference numbers. The circuits of FIGS. 3 and 6 function in a like manner excepting the step-wise incrementation of sensitivity control 66. By virtue of the additional component AND gate 100, the inputs of which are the output of dual decade counter 54 and the count1 output 102 of the binary counter 74, the gain sensitivity of amplifier 64 is limited to the gain necessary to permit threshold detector 68 to sense the ultrasound echo reflected back from the first fat layer interface 32 as shown in FIG. 2. The advantage of limiting the gain sensitivity of amplifier 64 in such a manner can be explained by reference to FIG. 2.

FIG. 2 shows probe 14 firmly applied to the animal outer skin 18 perpendicular to interfaces 32 and 36. When so applied, the ultrasound reflections from said interfaces are reflected directly back to probe 14 with little or no angular displacement from the orthogonal axes of said interfaces. When the probe 14 is so applied the gain sensitivity of amplifier 64 as embodied in FIG. 3 will step-wise increase until the ultrasound echo from interface 36 is detected, resulting in a correct measurement of the backfat width. If reasonable care is taken in placing probe 14 on the outer skin 18 of the animal, accurate measurements are easily obtained. However, in the event that probe 14 is placed so that the ultrasound echoes from interfaces 32 and 36 are displaced from the orthogonal axes of their planes, erroneous backfat depth measurements are possible with the embodiment shown in FIG. 3. Such erroneous measurements are attributable to random interfaces accruing within the animal tissue. When the probe 14 is poorly positioned, it is possible that the ultrasound echoes from interface 36 will be reflected to a position on the animal skin 18 that is sufficiently horizontally displaced from probe 14 so that excessive amplification by amplifier 64 is necessary to detect the displaced echo. Because of non-homogeneity in certain animal tissues a sensing of spurious echoes mistakenly for interface 36 is possible. The reason these spurious interfaces are mistakenly detected for interface 36 in the eembodiment of FIG. 3, is that the gain sensitivity of amplifier 64 is step-wise increased until the second echo is detected by threshold detector 68. The problem of excessive gain sensitivity by amplifier 64 when probe 14 is improperly positioned is eliminated in the embodiment of FIG. 6 by limiting the gain sensitivity to the level necessary to detect the first interface 32. Because of the short distance from the animal skin 18 to the first interface 32 the positioning of probe 14 with respect to the orthogonal axis of interface 32 is less critical than the positioning of probe 14 with respect to the orthogonal axis of interface 36. In that the amplitude of the reflected echo from interface 36 and that from interface 32 are substantially the same, it is possible to key or limit the gain sensitivity of amplifier 64 to that of interface 32. Thus, when the echo from interface 32 is detected, the detection of interface 36 becomes a function of probe placement 14 instead of amplifier sensitivity. Because the sensitivity of amplifier 64 is so limited, a mistaken detection of spurious interfaces for interface 36 becomes impossible, and so minimizes the degree of care necessary in the placement of probe 14 on the animal skin 18. In operating the backfat meter as embodied in FIG. 6, an accurate measurement may be obtained by merely placing probe 14 against animal skin 18 and adjusting its placement until a measurement is obtained.

Referring to FIG. 6, it can be seen that the addition of AND gate 100 and its corresponding connections to the embodiment of FIG. 3 serves to limit the gain sensitivity of amplifier 64 to the level necessary to detect the first interface 32. As shown, the count1 output 102 of binary counter 74 is inverted and applied to one input of AND gate 100 so as to inhibit the step-wise incrementation of sensitivity control 66 by output 58 of decade counter 54 after the detection of interface 32. It should be noted that AND gate 100 is designed so that its inherent delay properly inhibits the step incrementation of sensitivity control 66 during the reset cycle of binary counter 74.

As previously described in the embodiment of FIG. 3, binary counter 74 is reset each time decade counter 54 times out before the occurrence of an output at 80 of binary counter 74 or the detection of the second interface 36. The operation of the detection circuitry as embodied in FIG. 6 can be further explained by reference to FIG. 5. As explained earlier FIG. 5 represents one possible mode of operation of the embodiment of FIG. 3. In this mode the sensitivity control voltage represented by waveform 84 is step-wise incremented until during time period 3 the first and second echoes from the interfaces 32 and 36, respectively, are detected by threshold detector 68 during the same cycle. It is also seen that during time period 2, the first interface 32 is detected but the second interface 36 is not, a result which is likely to occur when the position of probe 14 on the animal skin 18 is poor. It should be realized, however, that given an adequate placement of probe 14 during time period 2, the second interface 36 could also have been detected. As evidenced by waveform 84 during time period 3, the embodiment shown in FIG. 3 causes a step-wise incrementation of the sensitivity control voltage during the next cycle of operation. In contrast, the embodiment of FIG. 6 inhibits this incrementation so that the sensitivity control voltage level 84 of time period 3 remains the same as that of time period 2. As noted previously, the detection of interface 36 as shown by pulse 90 during time period 3 then becomes a function of the positioning of probe 14. In this configuration the circuit shown in FIG. 6 will continue to cycle with the gain sensitivity of amplifier 64 keyed to the first fat layer as the operator manipulates the positioning of probe 14 until the second layer is detected, at which point the indicator light 76 alerts the operator that a valid measurement is appearing at the display outputs 56.

It will be seen that the embodiment of FIG. 6 effectively eliminates the possibility of erroneous backfat measurements due to improper probe placement, and thereby reduces the skill necessary to operate the backfat meter.

While the embodiment shown and described above is in terms of separate functional blocks, it will be understood by those skilled in the art that various functions could be combined or digitally implemented, for example by a microprocessor.

Numerous characteristics and advantages of the invention have been set forth in the foregoing description, together with details of structure and function of the invention, and the novel features thereof are pointed out in the appended claims. The disclosure, however, is illustrative only, and changes may be made in detail, especially in matters of shape, size, and arrangement of parts, within the principal of the invention to the full extent of the broad general meaning of the terms in which the appended claims are expressed.

I claim:

1. Ultrasonic measurement apparatus for measuring backfat thickness in animals, comprising:
    (a) means for transmitting ultrasonic energy pulses and for receiving return echo pulses, including a transducer for placement on the body of an animal to be tested;
    (b) amplifying means connected to said transducer means for amplifying echo pulses received by said transducer;
    (c) echo counting means connected to said amplifying means and operative to count amplified echo pulses having amplitude greater than a predetermined threshold value;
    (d) means for increasing the responsiveness of said ultrasonic measurement apparatus on succeeding transmitted pulses until a first predetermined number of echo pulses is counted by said echo counting means and for fixing the responsiveness of said apparatus at a substantially constant level after said first predetermined number is counted;
    (e) measurement and display means for measuring travel time of pulses in the animal's body, and operative in response to the counting of a second predetermined number of echo pulses at said constant level by said echo counting means to measure the travel time of the echo pulse corresponding to said second predetermined number and to display said measured travel time in terms of depth in the animal's body corresponding to said echo.

2. An ultrasonic measurement apparatus according to claim 1 wherein said means responsive comprises means for increasing the gain of said amplifying means on succeeding transmitted pulses.

3. An ultrasonic measurement apparatus according to claim 1 wherein said means responsive comprises means for increasing the amplitude of succeeding transmitted ultrasonic energy pulses.

4. An ultrasonic measurement apparatus according to claim 1 wherein said means responsive comprises means for lowering said predetermined threshold value.

5. Ultrasonic measurement apparatus for measuring backfat thickness in animals, comprising:
    (a) transducer means for transmitting ultrasonic energy pulses and for receiving return echo pulses including a transducer for placement on the body of an animal to be tested;
    (b) signal amplifying means coupled to said transducer to amplify echo pulses received from said transducer;
    (c) filter means connected to the output of said amplifying means for eliminating echo pulses not having a minimum predetermined amplitude, said filter means producing an output of echo pulses having an amplitude exceeding said minimum level;
    (d) first counter means for counting consecutive output echo pulses from said filter;
    (e) signal means coupled to said first counter means for producing a signal when a first predetermined count is reached by said first counter means;
    (f) second counter means for measuring the time from when a pulse is transmitted from said transducer to when a second predetermined count is reached by said first counter means;

(g) control means connected to said amplifier means for increasing the gain of said amplifier means by a predetermined magnitude when said pulses are transmitted until said first predetermined count is reached;

(h) reset means connected to said control means for resetting said gain to a predetermined minimum level when said second predetermined count is reached;

(i) blanking means connected to said control means for preventing said first and second counting means from being activated by pulses received by said transducer until a predetermined time period has passed so that reflections of the animal's skin will be ignored; and (j) conversion display means for converting said time measurement into a distance measurement and displaying said distance measurement in a form capable of human recognition.

6. Apparatus according to claim 5 wherein said control means includes a step-wise incrementation of gain such that said gain increases by a predetermined magnitude when a pulse is transmitted.

7. Apparatus according to claim 5 wherein said predetermined time period of said blanking means is long enough to prevent a first echo pulse received by said transducer to activate said first and second counting means.

8. Apparatus according to claim 7 wherein said predetermined time period is approximately 3-5 microseconds.

9. Apparatus according to claim 5 wherein said filter means includes detector means for converting A-C pulses to D-C pulses.

10. A method of indicating the thickness of backfat in an animal comprising the steps of:

(a) periodically transmitting ultrasonic energy pulses into the body of an animal;

(b) receiving the resulting return pulses;

(c) suppressing pulses which are received within a predetermined time from when the pulse is transmitted;

(d) amplifying the resulting filtered pulses by predetermined minimum gain factor;

(e) filtering out the amplified pulses which do not have a predetermined minimum amplitude;

(f) counting the pulses which have an amplitude above the predetermined minimum level;

(g) incrementally increasing the gain of said amplifier by a predetermined gain factor if the first pulse has not been counted;

(h) activate an indicator when two consecutive pulses are counted, to indicate that a second layer of backfat has been measured;

(i) measuring the time period from when a pulse was transmitted to when the indicator was activated and converting that time into a distance measurement which is then displayed in readable form;

(J) resetting the counter of step (f) to zero; and (k) resetting the gain factor of the amplifier to the level in step (f).

* * * * *